United States Patent
Hammer

(10) Patent No.: US 6,982,077 B2
(45) Date of Patent: Jan. 3, 2006

(54) LIQUID LIPSTICK

(75) Inventor: Alexander Hammer, Farmingdale, NY (US)

(73) Assignee: Lady Burd Exclusive Cosmetics, Farmington, NY (US)

( * ) Notice: Subject to any disclaimer, the term of this patent is extended or adjusted under 35 U.S.C. 154(b) by 533 days.

(21) Appl. No.: 10/280,365

(22) Filed: Oct. 24, 2002

(65) Prior Publication Data

US 2003/0082124 A1   May 1, 2003

Related U.S. Application Data

(60) Provisional application No. 60/346,100, filed on Oct. 24, 2001.

(51) Int. Cl.
*A61K 7/025* (2006.01)

(52) U.S. Cl. .......................... 424/64; 424/401

(58) Field of Classification Search .................. 424/64, 424/401
See application file for complete search history.

(56) References Cited

U.S. PATENT DOCUMENTS

| | | |
|---|---|---|
| 2,230,063 A | 2/1941 | Klimist et al. |
| 3,485,915 A | 12/1969 | Gerstein et al. |
| 4,963,591 A | 10/1990 | Fourman et al. |
| 5,002,762 A | 3/1991 | Bolich, Jr. Raymond E. |
| 5,073,573 A | 12/1991 | Martin et al. |
| 5,143,723 A | 9/1992 | Calvo et al. |
| 5,204,090 A | 4/1993 | Han |
| 5,324,506 A | 6/1994 | Calvo et al. |
| 5,650,139 A | 7/1997 | Nojima |
| 5,695,772 A | 12/1997 | Kanga et al. |
| 5,747,017 A | 5/1998 | Nichols et al. |
| 5,851,517 A * | 12/1998 | Mougin et al. .......... 424/78.02 |
| 6,001,374 A | 12/1999 | Nichols |
| 6,010,709 A | 1/2000 | Nichols |
| 6,027,739 A | 2/2000 | Nichols |
| 6,060,547 A | 5/2000 | Canter et al. |
| 6,063,391 A * | 5/2000 | Nanba et al. ................ 424/407 |
| 6,190,681 B1 | 2/2001 | Fishman |

FOREIGN PATENT DOCUMENTS

WO   WO 92/19215   11/1992

* cited by examiner

*Primary Examiner*—Thurman K Page
*Assistant Examiner*—Sharon Howard
(74) *Attorney, Agent, or Firm*—Robert D. Katz; Cooper & Dunham LLP

(57) ABSTRACT

The invention provides a liquid cosmetic suitable for application to the lips which comprises about 60% to about 80% of an alcoholic solvent; about 2% to about 20% of a vinyl acetate copolymer; about 0.10% to about 5% of a non-toxic glycol; about 0.09% to about 10% of cyclomethicone and aluminum magnesium hydroxide stearate; about 1% to about 7% decamethyl cyclopentasiloxane and trimethylsilicate; and about 0.01% to about 5% of a dye or pigment.

17 Claims, No Drawings

LIQUID LIPSTICK

This application claims the benefit of U.S. Provisional Application No. 60/346,100, filed on Oct. 24, 2001.

FIELD OF THE INVENTION

The present invention relates to lipstick products, and more particularly to liquid color products for application to the lips of a user.

BACKGROUND OF THE INVENTION

Lipsticks, of course, have been a staple article of any cosmetic kit or collection. Conventional lipsticks have wax bases, and the product tends to smear, or transfer when contacted by food, utensils, drinking glasses or cups, and cigarettes. Also, when a wearer kisses an acquaintance or companion, the lipstick may appear on that person's cheek or lips. This phenomenon may also soil clothing or accessories, and may necessitate frequent re-application of the lipstick, which may also lead to caking or cracking of the lipstick layer.

Others have attempted to formulate liquid lipsticks. Such products typically involve a volatile solvent, such as denatured alcohol, a film forming polymer base, a pigment, a cellulose ingredient, and possible other additives or ingredients. U.S. Pat. No. 5,143,723 (Calvo); U.S. Pat. No. 5,747,017 (Nichols); U.S. Pat. No. 6,190,681 (Fishman); U.S. Pat. No. 6,001,374 (Nichols); and U.S. Pat. No. 6,027,739 (Nichols), for example, give examples of liquid lipstick products. The disclosure of the foregoing patents is incorporated herein by reference.

Some such liquid lipstick products tend to cause a tingling, burning, or stinging sensation on the lips, which some users would find objectionable or undesirable. Other users find the existing liquid lipsticks unpleasant tasting, and would prefer a liquid lipstick with a more pleasant taste. Still others prefer cosmetics containing herbal ingredients, and it would be desirable to formulate a liquid lipstick which includes herbal ingredients, flavorings, or other additives.

SUMMARY OF THE INVENTION

The foregoing objects can be achieved and the disadvantages of prior liquid lipsticks can be overcome by providing a liquid cosmetic suitable for application to the lips which comprises about 60% to about 80% of an alcoholic solvent; about 2% to about 20% of a vinyl acetate copolymer; about 0.10% to about 5% of a non-toxic glycol; about 0.09% to about 10% of cyclomethicone and aluminum magnesium hydroxide stearate; about 1% to about 7% decamethyl cyclopentasiloxane and trimethylsilicate; and about 0.01% to about 5% of a dye or pigment.

Preferably, the liquid lipstick also includes natural herbs and other ingredients such as about 0.001% to about 1.00% of chamomile extract; about 0.01% to about 1.00% of jojoba oil; about 0.01% to about 1.00% of allantoin; about 0.01% to about 1.00% of aloe vera gel; and about 0.01% to about 1.00% of octylmethoxycinnamate.

In another embodiment, the invention provides a cosmetic kit comprising a liquid lipstick as set forth above, together with a liquid lipstick gloss comprising hydrogenated polyisobutenes, and petrolatum, and a liquid lipstick remover comprising water, glycerin and triethanolamine. A more complete understanding of the formulations of the present invention may be obtained by reviewing the following detailed description of the preferred embodiments.

DETAILED DESCRIPTION OF THE PREFERRED EMBODIMENTS

The present invention provides an easy to apply liquid alternative to solid wax-based lipsticks. It dries quickly, and has a desirable texture and feel for the wearer. It should not streak, rub off, or smear while swimming, drinking, smoking or kissing. It is waterproof and should not leave behind smears or marks on cups, glasses, cheeks, collars or dental work. Further, it should last well, and will not wear off while swimming or sleeping.

The liquid lipstick can be removed with a specially formulated remover, which can be sold separately, or as part of a kit. A lip gloss enhancer may also be used to make the finish more shiny or glossy-looking, or to give the liquid lipstick a "wet" look.

The liquid lipstick of the present invention in a broad sense includes as its principal ingredients a film forming polymer, a pigment, an alcoholic solvent, and one or more thickeners, humectants, moisturizers, and the like. Further, the liquid lipstick may advantageously contain natural flavors and herbs to improve the flavor, appearance, sensation on the lips, and dermatologic properties of the product.

As a film forming polymer, a number of polymers available from National Starch and Chemical, Bridgewater, N.J. may be used. Preferably, the polymer is Resyn 28-2930, a vinyl acetate/crotonates/vinyl neodecanoate copolymer, but such polymers as Amphomer, Dermacryl, Carboset, Lovocryl, among other polymers may also be used. The amount of polymer used varies on the particular properties of the polymer selected, but if the polymer is Resyn 28-2930, for example, as is preferred, approximately 2 to 20% should be used.

The solvent for the foregoing plasticizer or film former polymer should preferably be an alcohol approved for use in formulating cosmetics, such as denatured alcohol (ethanol), in the form of SDA-40 denatured alcohol. It can be used in an amount varying from approximately 60% to 80%. Other organic solvents which may be employed in addition to, or instead of denatured alcohol, such as stearyl alcohol, isostearyl alcohol, and fatty acids which are water-insoluble, such as lauric acid, stearic acid, myristic acid, palmitic acid, and lanolin fatty acid. Lanolin may also be used in the organic solvent.

The pigments and dyes used in the formulations in the present invention include standard pigments used in the industry, and identified by FD&C designations and D&C designations, but other listed and approved natural colors compatible with alcoholic solvents can be used. In addition, any non-toxic pigment certified by FD&C or D&C can be used. Preferably, a combination of pigments may be used to obtain the desired lipstick color. Such commonly used pigments as FD&C Yellow No. 5 (C69-002), Red No. 7 (C19-011), Red No. 22 (C14-6634), and Red No.21 (C14-032) may be used in amounts for each pigment from about 0.01% to about 6%, to obtain a desired red color, for example. Where alcohol-soluble pigments are used, dispersion in caster oil becomes unnecessary.

Others additives and ingredients enhance the liquid lipsticks of the present invention, including one or more humectants, viscosity builders, lubricants, UV protectors, herbs, and flavors.

The humectant may be propylene glycol, or another glycol or glycol polymer or sorbotol or glycerin. Preferably, the humectant is propylene glycol, and it should be present in an amount from about 0.10% to about 5%, with 1 to 2% more preferred.

The viscosity builder may include a mixture of Cyclomethicone (and) Aluminum Magnesium Hydroxide Stearate in an amount ranging from about 1% about 7%, or more preferably about 2.5% to about 4%. The viscosity builder or thickener may include other silicone polymers available from GE Silicones including cyclomethicone, dimethicone and mixtures thereof, or other GE silicone polymers suitable for personal use. Alternatively, lanolin alcohol or hydrogenated castor oil may be used. Preferably, the viscosity builder is Gilugel Sil-5, available from Giulini Corporation, New Rochelle, N.Y.

The composition of the present invention advantageously includes lubricants such as silicone polymers. Preferably, a cosmetic formulation product including decamethyl cyclopentasiloxane (and) trimethylsiloxysilicate, in an amount ranging from about 1 to about 7% can be used. The lipstick may include additional lubricants, such as the natural ingredient jojoba oil available from Desert Whale in Tucson, Ariz. Other useful lubricants include silicone or mineral oil.

Lip coloring formulations can also include ingredients to moisturize or sooth the lips of the user, which may be dry, chapped or sore. For this purpose, the liquid lipstick of the present invention may include moisturizing agents including Aloe Vera Gel (available from Aloe Corporation, Broomfield, Colo.), Allantoin (Universal Preserv-A-Chem, Edison, N.J.), extract of chamomile and avocado extract (both available from Active Organics). Octyl Methoxycinnanate (ISP/Van Dyle, Belleville, N.J.) adds ultraviolet protection to the formula. The amount of each such ingredient may range from about 0.001 to 0.1%, but they may be omitted altogether from the formulation.

Various natural flavors and herbs known to those of ordinary skill may be used to enhance the flavor of the lipstick to make it more pleasant for the user to apply. For example, natural flavor 127-029 from Technology Flavors & Fragrances, Amityville, N.Y., and Sweet Herb (Stevia) may be added as optional ingredients.

The present invention advantageously can be used with a lip gloss to enhance its appearance. As detailed more particularly in Example II, the lip gloss includes a mixture of hydrogenated polyisobutenes of varying molecular weights, such as Panalene H-300E and Panalene L-14E, in amounts ranging from 35 to 60% for either ingredient. The lip gloss also includes about 1 to 10% of petrolatum, about 1 to 5% of polyethylene (New Face Technologies, Piscataway, N.J.), and about 0 to 2% Vitamin E, and 0 to 2% BHT as a preservative. The mixture may include a pigment or colorant, but preferably it omits colorants, and provides a clear lip gloss. To make this composition, heat the polyethylene in the Panalenes gently until polyethylene melts and the mixture is homogenous, and then add remaining ingredients.

The present invention also provides a remover for the liquid lipstick, which advantageously avoids the use of detergents. Instead, it contains 80 to 95% water; 0 to 5% cellulose gum; 0.5 to 2.5% parabens (preferably methyl propyl parabens), about 1 to about 5% glycerin, and about 2 to about 10% triethanolamine (to adjust the pH).

It should be apparent to those of ordinary skill that many modifications may be made without departing from the spirit of the invention. It is therefore intended that the invention be defined by the claims. Likewise, the following examples are meant to be illustrative of the practice of the invention, and is not intended to limit its scope.

EXAMPLE I

| INGREDIENT | AMOUNT (%) |
|---|---|
| SDA-40 (Denat. Alcohol) | 72.19 |
| VA/Crotonates/VinylNeodecanoate Copolymer | 10.33 |
| Propylene Glycol | 1.29 |
| Cylomethicone (and) Aluminum Magnesium Hydroxide Stearate | 0.21 |
| Decamethyl Cyclopentasiloxane (and) Trimethylsiloxysilicate | 3.28 |
| Extract of Chamomile | 0.001 |
| Avocado Extract | 0.001 |
| Jojoba Oil | 0.001 |
| Allantoin | 0.001 |
| Aloe Vera Gel | 0.001 |
| Octyl Methoxycinnamate | 0.001 |
| FD&C Yellow #5 C69-002 | 1.26 |
| Red 7 C19-011 | 1.65 |
| Red 22 C14-6634 | 5.25 |
| Red 21 C14-032 | 4.45 |
| Natural Flavor | 0.09 |
| Sweet Herb | 0.001 |

Resyn 28-2930 was dissolved in SDA-40 denatured alcohol, and the remaining ingredients were blended in to obtain a homogenous mixture. The liquid lipstick had the desired red color, applied easily, dried quickly, and did not rub off or smear. It had a pleasant taste, did not sting or burn upon application, and would not wash off with water. Its appearance could optionally be enhanced with the lip gloss of Example II.

EXAMPLE II

| INGREDIENT | AMOUNT (%) |
|---|---|
| Panalane H-300E (hydrogenated polyisobutene) | 54.13 |
| Panalene L-14E (hydrogenated polyisobutene) | 39.10 |
| Petrolatum (Vaseline) | 4.19 |
| Polyethylene | 2.33 |
| Vitamin E | 0.20 |
| BHT (preservative) | 0.50 |

The liquid lipstick and optional lip gloss could be removed using the liquid lipstick remover specially formulated for use in the present invention. A kit will include the liquid lipstick, the lip gloss, and the lipstick remover.

EXAMPLE III

| INGREDIENT | AMOUNT (%) |
|---|---|
| Water | 92.0 |
| Gum (cellulose) | 0.85 |
| Methyl Propyl Paraben (paraben combinations) | 1.0 |
| Glycerin | 1.5 |
| Triethanolamine (neutralizer - adjust pH) | 4.0 |

I claim:
1. A liquid lipstick comprising:
about 60% to about 80% of an alcoholic solvent;
about 2% to about 20% of a vinyl acetate copolymer;
about 0.10% to about 5% a glycol humectant;

about 0.09% to about 10% of cyclomethicone and aluminum magnesium hydroxide stearate;

about 1% to about 7% decamethyl cyclopentasiloxane and trimethylsilicate; and about 0.01% to about 5% of a dye or pigment.

2. A liquid lipstick in accordance with claim 1 wherein the dye or pigment is an FD&C or D&C dye or pigment.

3. A liquid lipstick in accordance with claim 1 wherein the dye or pigment is FD&C Yellow No. 5, Red No. 7, Red No. 21, Red No. 22, or mixtures thereof.

4. A liquid lipstick in accordance with claim 1, additionally comprising:

about 0.001% to about 1.00% of chamomile extract;
about 0.01% to about 1.00% of jojoba oil;
about 0.01% to about 1.00% of allantoin;
about 0.01% to about 1.00% of aloe vera gel; and
about 0.01% to about 1.00% of octylmethoxycinnamate.

5. A liquid lipstick in accordance with claim 1 additionally comprising about 0.01% to 0.50% of natural flavor.

6. A liquid lipstick in accordance with claim 4 additionally comprising about 0.01% to 0.50% of natural flavor.

7. A liquid lipstick in accordance with claim 1 additionally comprising about 0.01% to about 0.5% of sweet herb.

8. A liquid lipstick in accordance with claim 4 additionally comprising about 0.01% to about 0.5% of sweet herb.

9. A liquid lipstick in accordance with claim 6 additionally comprising about 0.01% to about 0.5% of sweet herb.

10. A liquid lipstick in accordance with claim 1 wherein the vinyl acetate copolymer is a vinyl acetate/crotonate/vinyl neodecanoate copolymer.

11. A liquid lipstick, comprising:

about 60% to about 80% of an alcoholic solvent;
about 2% to about 20% of a vinyl acetate copolymer film former;
about 0.1% to about 5% of a glycol humectant;
about 0.05% to about 10% of a thickener including cyclomethicone and aluminum magnesium hydroxide stearate;
about 1% to about 7% of a cyclopentasiloxane and silicate lubricant; and
about 0.01% to about 10% of a pigment.

12. A liquid lipstick in accordance with claim 11, additionally comprising about 0 to 1% extract of chamomile, about 0 to 1% avocado extract, about 0 to 1% jojoba oil, about 0 to 1% allantoin, about 0 to 1% aloe vera gel, and about 0 to 1% of octylmethoxycinnanate.

13. A liquid lipstick in accordance with claim 12, additionally comprising about 0 to 1% of a natural flavor and about 0 to about 1% of a sweet herb.

14. A liquid lipstick in accordance with claim 13 wherein the dye or pigment is an FD&C or D&C dye or pigment.

15. A cosmetic kit comprising:

a liquid lipstick in accordance with claim 1;
a liquid lipstick gloss comprising hydrogenated polyisobutylene and petrolatum; and
a liquid remover comprising water, glycerin and trimenthanolamine.

16. A cosmetic kit comprising:

a liquid lipstick in accordance with claim 4;
a liquid lipstick gloss comprising glycerin and trimenthanolamine; and
a liquid remover comprising hydrogenated polyisobutylene and petrolatum.

17. A lip gloss comprising hydrogenated polyisobutylene and petrolatum.

* * * * *